United States Patent
Drope et al.

(10) Patent No.: US 6,271,414 B1
(45) Date of Patent: Aug. 7, 2001

(54) PROCESS FOR THE ISOMERIC SEPARATION OF ISOCYANATES

(75) Inventors: Rüdiger Drope, Köln; Dieter Grenner, Leverkusen; Hartmut Hetzel, Köln; Hans-Peter Schal, Dormagen; Gerhard Wegener, Mettmann, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/297,350
(22) PCT Filed: Oct. 24, 1997
(86) PCT No.: PCT/EP97/05884
§ 371 Date: Apr. 29, 1999
§ 102(e) Date: Apr. 29, 1999
(87) PCT Pub. No.: WO98/19993
PCT Pub. Date: Mar. 14, 1998

(30) Foreign Application Priority Data

Nov. 6, 1996 (DE) .................................. 196 45 659

(51) Int. Cl.⁷ .................................. C07C 251/00
(52) U.S. Cl. .................................. 560/352; 560/336
(58) Field of Search .................................. 560/336, 352

(56) References Cited

U.S. PATENT DOCUMENTS

| | | | |
|---|---|---|---|
| 2,831,012 | * 4/1958 | Bernard | 560/352 |
| 3,144,474 | * 8/1964 | Kantyka et al. | 560/352 |
| 3,217,024 | * 11/1965 | Park et al. | 560/352 |
| 3,232,069 | * 2/1966 | Hawkins | 560/352 |
| 3,591,617 | * 7/1971 | Buchsbaum | 560/352 |
| 3,777,892 | 12/1973 | Thijssen et al. | 210/178 |
| 3,872,009 | 3/1975 | Thijssen et al. | 210/178 |
| 4,004,886 | 1/1977 | Thijssen et al. | 23/273 F |
| 4,246,187 | * 1/1981 | Yabroff | 560/352 |
| 4,316,368 | 2/1982 | Van Pelt et al. | 62/542 |
| 4,430,104 | 2/1984 | Van Pelt et al. | 62/123 |
| 4,459,144 | 7/1984 | Van Pelt et al. | 62/541 |
| 4,499,023 | 2/1985 | Mitrowsky et al. | 260/453 SP |
| 4,787,985 | 11/1988 | Roodenrijs et al. | 210/772 |
| 5,783,727 | * 7/1998 | Parron et al. | 560/352 |

OTHER PUBLICATIONS

Chem. Abstracts, vol. 102, No. 6, Feb. 11, 1995, Abstract No. 47895k, Fischer et al.

Chem. Abstracts, vol. 100, No. 24, Jun. 11, 1984, Abstract No. 192323k, Pogodin et al.

* cited by examiner

Primary Examiner—Paul J. Killos
Assistant Examiner—Taylor V Oh
(74) Attorney, Agent, or Firm—Joseph C. Gil; Lyndanne M. Whalen

(57) ABSTRACT

A process is described for obtaining pure isocyanate isomers from a mixture of isocyanate isomers by suspension crystallization and the isolation of isomerically pure crystals, which is characterized in that, prior to the isolation of the crystals, 5 to 40% by weight of the crystals produced are remelted while simultaneously increasing the temperature of the crystal slurry by 4.5 to 9° C.

11 Claims, 1 Drawing Sheet

PROCESS FOR THE ISOMERIC SEPARATION OF ISOCYANATES

The present invention relates to a process for separating isocyanate isomers by suspension crystallization. During its production, tolylene diisocyanate (TDI) is generally obtained in the form of a mixture of 80% by weight of 2,4-tolylene diisocyanate (2,4-TDI) and 20% by weight of 2,6-tolylene diisocyanate (2,6-TDI).

Since the properties of the isomers are different, and in particular their reaction rate in the presence of polyols during the polyaddition reaction for the production of polyurethanes, both pure 2,4-TDI (T100) and an isomer mixture with a reduced content of 2,4-TDI of 65 to 68% by weight (T65) are used industrially in addition to the use of the isomer mixture (T80) resulting from the production process.

Since the molecular structures of the two isomers differ in geometry, the phase diagram displays a considerable decrease in the freezing point on the 2,4-TDI side. The freezing point of the 80:20 isomer mixture is 13.6° C. and that of the 65:35 isomer mixture is only 5° C. In the entire mixing range between 100 and 65% by weight of 2,4-TDI more than 99% pure T100 always crystallizes on slowly cooling the mixtures to below the liquidus temperature.

A similar situation applies to diphenylmethane diisocyanate (MDI). This is obtained in the form of a mixture of 4,4'-MDI and 2,4'-MDI in a ratio of between 70:30 and 90:10. The melting point of 4,4-MDI is 40° C. and that of a mixture of 60% of 4,4-MDI and 40% of 2,4-MDI is between 21 and 23° C., depending on the additional content of up to 2% of 2.2-MDI in the mixture.

Crystallization from the corresponding mixtures is therefore a suitable process for separating the isomers.

The static crystallization process is the most commonly used isomer separation process, in which the isomer to be isolated is deposited on stationary cooled surfaces, subsquently separated from the "mother liquor" and remelted.

Suspension crystallization processes can generally be carried out in an energetically more favourable manner and with a more efficient separation effect than static crystallization processes, if so-called wash columns according to U.S. Pat. Nos. 3,777,892 and 3,872,009 are used for separating and melting the crystal phase.

Such suspension crystallization processes are basically known in particular for aqueous systems, such as for example for the removal of water from foodstuff liquids, as described in U.S. Pat. Nos. 4,004,886, 4,316,368, 4,430,104 and 4,459,144. In addition, U.S. Pat. No. 4,787,985 proposes suspension crystallization processes for the purification of chemicals.

A common feature of all these processes is that they comprise (per stage in multi-stage crystallization processes) a crystallization tank in which crystals are frozen out by the removal of heat, a recrystallization tank in which larger crystals grow at the expense of smaller crystals, and a filter in which the crystals are separated from the mother liquor. At least the filter of the last stage is in the form of a wash column.

Due to the exceedingly low solid phase solubility of 2,6-TDI in 2,4-TDI and of 2,4-MDI in 4,4-MDI, single-stage suspension crystallization processes are in principle suitable for the separation of isomers.

Problems do however arise during recrystallization in the recrystallization tank, i.e. during crystal enlargement, due to the low diffusion rate of the molecules in the liquid phase. Since the mass transfer at the crystal surface is determined by the diffusion rate in the liquid interfacial layer, uneconomically long recrystallization times would be necessary together with correspondingly large recrystallization tanks.

Problems are also caused by the longitudinal, almost acicular, 2,4-TDI crystals, which not only produce a major reduction in the recrystallization rate but are also difficult to separate in the wash column.

It has now been found that the suspension crystallization process can be advantageously used for the separation of isocyanate isomers, and in particular TDI and MDI isomers, if prior to the introduction of the crystal slurry into the wash column, 5 to 40, preferably 10 to 40, and most preferably 15 to 30% by weight of the isomer crystals to be isolated are remelted while simultaneously increasing the temperature of the crystal slurry by 4.5 to 9° C.

BRIEF DESCRIPTION OF THE DRAWING

The present invention thus relates to a process for obtaining pure isocyanate isomers, and in particular 2,4-TDI and 4,4-MDI, from a corresponding mixture of isomers by suspension crystallization and isolation of the pure crystals, which is characterized in that prior to the isolation of the crystals, 5 to 40% by weight of the crystals produced are remelted while simultaneously increasing the temperature of the crystal slurry by 4.5 to 9° C.

Preferably the crystals are remelted in a mixing tank which is arranged upstream of the wash column and in which a temperature is maintained which is 4.5 to 9° C. higher than the temperature of the crystallizer. By introducing the crystal slurry into the mixing tank at an elevated temperature a specific thermal stress is produced which particularly favours the dissolution of smaller crystals and thus compensates for the low recrystallization rate of the isomerically pure isocyanate crystals.

Figure 1:
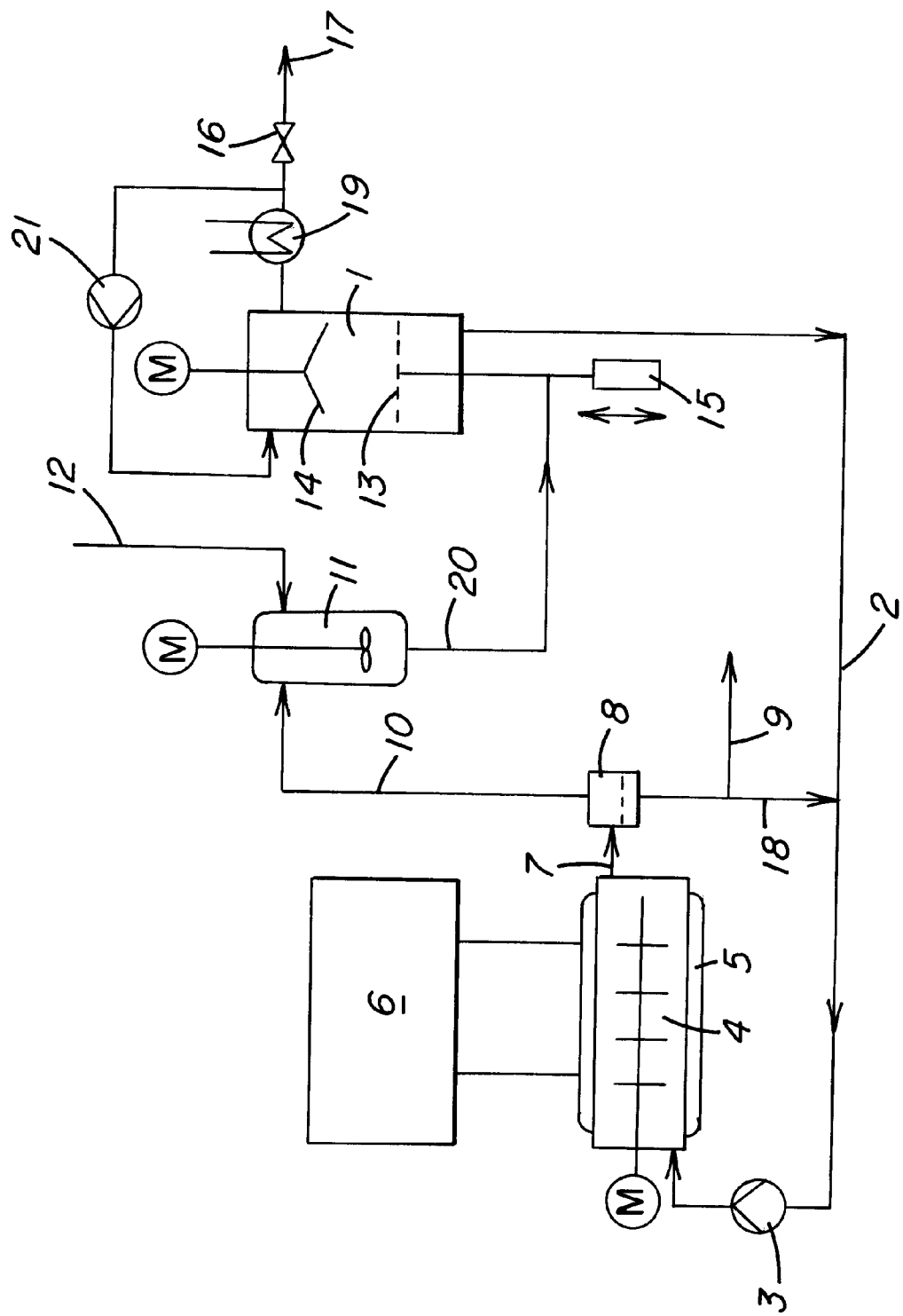

The mixing tank into which the starting isomer mixture is preferably also introduced, thus replaces the recrystallization tank used in conventional suspension crystallization processes.

Depending on the size of the mixing tank and thus the residence time therein, crystal enlargement can additionally occur as a result of recrystallization, although it is preferable according to the invention to provide a mixing tank with a small volume and a relatively short residence time. Most preferably the mixing tank is of such a size that the residence time of the crystal slurry in the mixing tank is between 1 and 15 minutes, and most preferably between 5 and 10 minutes.

It is essential according to the invention to introduce heat into the mixing tank in order to maintain the elevated temperature and to melt the crystals. The heat can be introduced either indirectly via jacket heating around the mixing tank or preferably by correspondingly heating the starting isomer mixture also to be introduced into the mixing tank.

The mother liquor with a reduced content of isomerically pure isocyanate is discharged through a filter arranged between the crystallizer and the mixing tank.

Preferably a mixture of 80% by weight of 2,4-TDI and 20% by weight of 2,6-TDI is used as the starting isomer mixture. The starting isomer mixture introduced into the mixing tank preferably has a temperature of between 17 and 30° C., most preferably between 18 and 24° C.

The liquid phase with a reduced content of 2,4-TDI still contains 65 to 69% by weight, and preferably 66 to 68% by weight, of 2,4-TDI. A temperature of between 5 and 7° C. is maintained in the crystallizer.

At the top of the wash column, 2,4-TDI having a concentration of higher than 99%, preferably higher than 99.8%, and most preferably higher than 99.9%, and a temperature of at least 22° C. is removed.

The mother liquor removed from the wash column is recycled into the crystallizer.

For the separation of MDI isomers, a starting isomer mixture of 70 to 90% of 4,4'-MDI and 30 to 10% of 2,4'-MDI is preferably used. The starting isomer mixture is preferably introduced into the mixing tank at a temperature of 30 to 45° C. The liquid having a reduced content of 4,4'-MDI preferably still contains 50 to 60% of 4,4'-MDI. The temperature in the crystallizer is preferably 15 to 21° C.

According to another variant of the invention the latter also relates to a process for the separation of isocyanate isomers, in particular TDI and MDI isomers, by suspension crystallization and the isolation of isomerically pure crystals, which is characterized in that after issuing from the crystallizer, the crystal suspension is mixed with the starting isomer mixture, the latter being added at such a temperature that the mother liquor formed has a relative degree of undersaturation of 4 to 20%, preferably 7 to 17%.

The mother liquor formed is understood to be the mixture of the mother liquor introduced from the crystallizer, which has the same temperature as the crystallizer and a residual concentratrion of the isomer obtained in the form of crystals, and the starting isomer mixture introduced, which has a higher concentration. This mixture should have a concentration which is 4 to 20% lower than the equilibrium concentration corresponding to the mixing temperature, according to the liquidus curve of the phase diagram. In this mother liquor produced in the mixing tank by mixing, the crystals initially still have the lower temperature of the crystallizer. Smaller crystals are dissolved in the undersaturated mother liquor. Larger crystals are initially dissolved to a partial extent, as a result of which the concentration of mother liquor in the interfacial layer increases. At the same time the larger crystals withdraw such an amount of heat from the mother liquor surrounding them that the latter becomes supersaturated. The larger crystals grow again.

The greater the degree of undersaturation, the larger number of small crystals are dissolved; the lower the degree of undersaturation, the higher is the rate of growth of larger crystals. The optimum degree of under-saturation depends on the crystal size distribution produced in the crystallizer. This can be determined by means of simple preliminary tests by varying the temperature of the starting isomer mixture introduced in relation to the separating capacity of the washer.

The invention is explained in more detail below by means of the attached FIG. 1:

Mother liquor recirculated from the wash column 1 via line 2 by means of pump 3 is introduced into the crystallizer 4, the cooling jacket 5 of which is cooled by means of cooling device 6. The crystal slurry passes from the crystallizer 4 via line 7 into filter 8, where mother liquor of a reduced concentration is discharged via line 9. The crystal slurry having a correspondingly increased content of crystals is introduced via line 10 into mixing tank 11, in which a higher temperature prevails than in the crystallizer 4. In addition, the starting isomer mixture is introduced via line 12 into the mixing tank 11. The temperature of line 12 is sufficiently high to ensure that the temperature in the mixing tank is maintained. Alternatively the mixing tank 11 can be provided with a jacket heating. The mother liquor which issues from the mixing tank 11 and whose content of smaller crystals has been melted, passes via line 20 into the wash column above mesh bottom plate 13. The mother liquor passes through the mesh bottom plate 13 and is recycled into the crystallizer via line 2. The mesh bottom plate 13 is periodically moved towards the crystal scraper 14 by means of the reciprocating piston pump 15, in which process the mother liquor is discharged under pressure from the space above the mesh bottom plate 13 and the crystals are compacted. The scraper 14 removes the same quantity of crystals from the compacted crystal block as are subsequently added by the mesh bottom plate 13. The crystals are melted in heat exchanger 19 and discharged via valve 16 and line 17. The melt issuing from the heat exchanger 19 is partially recycled via pump 21 into the top of the wash column so that a temperature close to the melting point is maintained at the top of the wash column. The valve 16 maintains at least such a high pressure above the mesh bottom plate 13 that some of the melted crystals, i.e. the pure liquid, are passed through the compacted crystal block under pressure in order to wash off any mother liquor still adhering thereto. Some of the mother liquor removed via filter 8 can be recycled into crystallizer 4 via line 18, in order to control the solids content in crystallizer 4.

EXAMPLE

In a pilot unit according to FIG. 1, 100 parts of TDI 80/20 having a temperature of 25° C. are introduced per hour via line 12. 60.6 parts of TDI 67/33 are discharged per hour via line 9 and 39.4 parts of 99.9% 2,4-TDI per hour via line 17. In crystallizer 4 a temperature of 6.3° C. is maintained. The crystal content in the crystallizer 4 is kept at 25% by weight by partially recycling the mother liquor removed by means of filter 8 via line 18. After removing some of the mother liquor via filter 8 the crystal slurry, which also has a temperature of 6.3° C., enters the mixing tank 11. The crystal slurry issuing from the mixing tank 11 and introduced into the wash column has a temperature of 11.5° C. and a liquid phase concentration of 76.5% by weight of 2,4-TDI. The residence time in the mixing tank 11 is 10 minutes and the residence time in crystallizer 4 is 120 minutes.

What is claimed is:

1. A process for obtaining pure isocyanate isomers from a mixture of isocyanate isomers by suspension crystallization and the isolation of isomerically pure crystals, characterized in that prior to the isolation of the crystals, 5 to 40% by weight of the crystals produced are remelted while simultaneously increasing the temperature of the crystal slurry by 4.5 to 9° C.

2. A process according to claim 1, characterized in that 10 to 24% by weight of the crystals produced are melted.

3. A process according to claim 1, characterized in that the processes of melting and increasing the temperature of the crystal slurry are carried out in a mixing tank which is arranged between the crystallization tank and the separating device and into which heat is introduced.

4. A process according to claim 1, characterized in that the starting mixture is introduced into the mixing tank.

5. A process according to claim 3, characterized in that the residence time in the mixing tank is 1 to 15 minutes.

6. The process of claim 2 in which melting and increasing the temperature of the crystal slurry are carried out in a mixing tank arranged between the crystallization tank and the separating device into which heat is introduced.

7. The process of claim 6 in which the mixture of isocyanate isomers is introduced into the mixing tank.

8. The process of claim 1 in which the mixture of isocyanate isomers is composed of 80% by weight 2,4-toluene diisocyanate and 20% by weight 2,6-toluene diisocyanate.

9. The process of claim 8 in which liquid phase discharged has a 2,4-toluene diisocyanate of from 65 to 69% by weight.

10. The process of claim 4 in which the residence time of isocyanate isomer mixture in the mixing tank is from 1 to 15 minutes.

11. The process of claim 7, in which the residence time of isocyanate isomer mixture in the mixing tank is from 1 to 15 minutes.

* * * * *